United States Patent [19]

Karlsson et al.

[11] Patent Number: 5,714,074
[45] Date of Patent: Feb. 3, 1998

[54] METHOD AND APPARATUS FOR LIQUID CHROMATOGRAPHY

[75] Inventors: Kjell Karlsson; Karl-Gunnar Hellström, both of Uppsala, Sweden

[73] Assignee: Pharmacia Biotech AB, Uppsala, Sweden

[21] Appl. No.: 537,819

[22] PCT Filed: Apr. 25, 1994

[86] PCT No.: PCT/SE94/00362

§ 371 Date: Sep. 24, 1996

§ 102(e) Date: Sep. 24, 1996

[87] PCT Pub. No.: WO94/25134

PCT Pub. Date: Nov. 10, 1994

[30] Foreign Application Priority Data

Apr. 26, 1993 [SE] Sweden ............... 9301395

[51] Int. Cl.$^6$ ............................... B01D 15/08
[52] U.S. Cl. ............. 210/656; 210/198.2; 210/450; 96/101
[58] Field of Search ............ 210/635, 656, 210/659, 198.2, 450; 141/12, 73, 80; 95/82; 96/101

[56] References Cited

U.S. PATENT DOCUMENTS

| | | | |
|---|---|---|---|
| 3,487,938 | 1/1970 | Patterson | 210/198.2 |
| 3,966,609 | 6/1976 | Godbille | 210/198.2 |
| 4,228,007 | 10/1980 | Rausch et al. | 210/198.2 |
| 4,350,595 | 9/1982 | Gunkel | 210/198.2 |
| 4,497,711 | 2/1985 | Shepherd | 210/198.2 |
| 4,549,584 | 10/1985 | Morin et al. | 210/198.2 |
| 4,597,866 | 7/1986 | Couillard | 210/198.2 |
| 4,732,687 | 3/1988 | Müller et al. | 210/198.2 |
| 4,737,292 | 4/1988 | Ritacco et al. | 210/198.2 |
| 4,769,141 | 9/1988 | Couillard | 210/198.2 |
| 4,865,728 | 9/1989 | Larsson | 210/198.2 |
| 4,891,133 | 1/1990 | Colvin | 210/198.2 |
| 5,021,162 | 6/1991 | Sakamoto | 210/635 |
| 5,141,635 | 8/1992 | LePlans | 210/656 |
| 5,169,522 | 12/1992 | Shalon | 210/656 |
| 5,282,973 | 2/1994 | Mann | 210/656 |
| 5,610,322 | 3/1997 | Unger | 210/198.2 |

FOREIGN PATENT DOCUMENTS

| | | | |
|---|---|---|---|
| 0040663 | 9/1986 | European Pat. Off. | 210/198.2 |
| 3000475 | 7/1980 | Germany | 210/198.2 |
| 2238257 | 11/1990 | United Kingdom | 210/198.2 |

OTHER PUBLICATIONS

Patent Abstract of Japan No. 4-98156—Mar. 10, 1992 vol. 16, No. 330, P-1388.
Patent Abstract of Japan No. 02134562-A—May 23, 1990 Accession No. 90204516/27, 9027, abstract.

*Primary Examiner*—Ernest G. Therkorn
*Attorney, Agent, or Firm*—Birch, Stewart, Kolasch & Birch, LLP

[57] ABSTRACT

In a method of filling a liquid chromatographic column with particulate separation medium, a liquid suspension of the particulate separation medium is introduced into one end of the column, wherein the column is closed at one end with a first filter, so that the particles will be retained by the filter while the liquid passes therethrough. After terminating the filling process, the other end of the column is closed with a second filter. According to the invention, the particle suspension is delivered via an inlet element which can be moved axially in relation to the end of the column an in which the second filter in mounted. During the filling process, the inlet element and the filter are held in a position in which the particle suspension is able to pass from the upper side of the filter and past its side-edge and into the interior of the column. After completion of the filling process, the inlet element is moved towards the end of the column, while maintaining liquid pressure, to a position in which by-passage of the filter is prevented, whereafter the inlet element is fixed in this position. The invention also relates to a column for carrying out the method.

13 Claims, 2 Drawing Sheets

1

METHOD AND APPARATUS FOR LIQUID CHROMATOGRAPHY

The present invention relates to a column for liquid chromatography, which includes a column tube intended to be filled with a separation medium, and inlet and outlet means. The invention also relates to a method of filling such a column tube with separation medium.

In order for a chromatographic column to be able to separate biological substances effectively, it is usual to pack fine particles of separation material as tightly and as uniformly as possible in the column tube. Filling of the column, or column packing as it is often referred to, is normally effected by closing one end of the column with an outlet means which includes a filter element, and pumping a liquid suspension of the particles under pressure into the other end of the column. Whereas the pumped liquid is able to pass through the filter element essentially unobstructed, the particles are retained by the filter element, so as to build up a particle bed along the length of the tube. As the column tube is filled, the particles are pressed out towards the wall of the tube and the particle bed obtains a stable compaction state with the particles well distributed, this state being maintained during the whole of the filling process.

However, when the column tube has been filled with particles and pumping of the liquid suspension is terminated to enable an inlet element to be fitted to the filling-end of the tube, the stable restraining force in the particle bed is partially lost, resulting in expansion of the particle bed. Consequently, when the column tube is once again placed under pressure, disturbing heterogeneities or irregularities are liable to occur in the particle bed, such as the formation of channels and dead volumes.

Numerous attempts have been made to solve this problem. For instance, EP-A-0040663 suggests that the inlet element is provided with a spring construction which will maintain the column bed under pressure and therewith improve bed stability. A similar construction based on the effect produced by a pressure plunger is described in DE-A-3021366 and U.S. Pat. No. 4,350,595. DE-A-3000475 describes a column having a flexible wall which stabilizes packing of the particles by radial compression of the column packing. A column-filling device including a pressure plunger which functions to compress the bed during the actual filling process but which is then removed is described in U.S. Pat No. 4,549,584. The construction that, at present, has been best established commercially for improving bed stability is one in which the inlet element is provided with a hand-adjustable plunger arrangement or the like, for instance as described in U.S. Pat. No. 4,737,292. A slightly different concept is proposed in U.S. Pat. No. 4,732,687, which describes the use of a perforated plate which is mounted in the upper part of the column and through which a particle slurry can be introduced but which is intended essentially to prevent expansion of one particle bed when the filling device is removed. Further variants are described in JP-A-4-98156, JP-A-2-134562 and GB-A-2,238,257.

All of these earlier proposed solutions involve complicated technical constructions and/or only provide partial compensation for the resultant stability without being able to re-establish the original degree of compaction and density of the packed particle bed.

Accordingly, an object of the present invention is to provide a column having an inlet part which, while being structurally simple, enables the original compactness/density of the particle bed to be maintained, so as to avoid completely those problems that are associated with a drop in pressure in the column bed and expansion of the column bed subsequent to filling the column. Another object of the invention is to provide a method for filling a column in accordance with this concept.

These and other objects of the invention and advantages afforded thereby, as made apparent in the following description, are achieved with a method and a column arrangement having the characteristic features set forth in respective claims 1 and 2 and described in more detail herebelow. Preferred embodiments of the invention are set forth in the depending claims.

The invention will now be described in more detail with reference to some particular exemplifying embodiments of a separation column constructed in accordance with the invention, and also with reference to the accompanying drawings, in which

DESCRIPTION OF THE PREFERRED EMBODIMENTS

Figure 1:
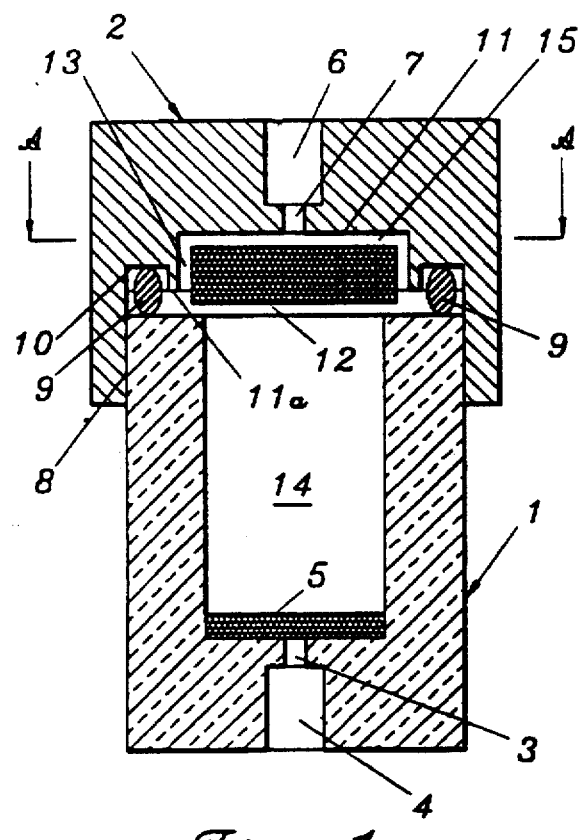
FIG. 1 is a longitudinal-sectioned view of one embodiment of the separation column with the inlet part shown in a column filling position.

The separation column illustrated in the drawings is comprised of a column tube 1, for instance made of glass, PEEK (a polyether-ether-ketone sold by ICI) or like material, and an inlet means in the form of a top element 2, made for instance of PEEK. The inlet means can be moved axially along the tube 1 and locked thereto, as will be described in the following. The bottom part of the tube 1 includes an outlet passage 3 which opens into a connecting recess or aperture 4 which is screw-threaded for instance (not shown). A bottom filter 5 is sealingly mounted on top of the outlet passage 3.

Similar to the bottom part of the tube, the top element 2 also has a connecting recess or aperture 6 (for instance screw-threaded) which includes an inlet passage 7 which opens into a central recess 8 in the bottom part of the top element 2. The inner diameter of the recess 8 corresponds to the outer diameter of the column tube 1, so that the top element 2 can be moved vertically, i.e. axially, in relation to the tube 1. A resilient seal 9, which in the illustrated case is an O-ring made of silicone rubber for instance, is received in an annular groove 10 provided in the bottom of the recess 8. The recess 8 is provided inwardly of the sealing groove 10 with a circular recessed-part 11 which is adapted to accommodate a top filter 12, made for instance of sintered PEEK. For reasons that will be readily apparent from the following description, the recessed-part 11 has a depth which is slightly smaller than the thickness of the filter 12. Furthermore, the diameter of the recessed-part 11 in relation to the filter is such as to enable the filter to be fixated in any desired position in the recessed-part by virtue of a force-fit, and so that the filter can only be moved vertically in the recessed-part by applying to the filter a force which is greater than the force to which the filter is subjected during filling of the column. Arranged around the periphery of the recessed-part 11 are a number, in the illustrated case six, radial slots or channels 13 which connect the bottom of the recessed-part 11 with the space below the sealing groove 10, and therewith also with the column tube interior 14. As will be readily understood from the following description of the manner in which the column works, the configuration of these channels can be varied within wide limits, for instance with regard to both number, peripheral extension and radial depth.

When filling the column tube 1 with packing material, the top element 2 will have the position shown in FIG. 1, in which it rests against the uppermost part of the tube 1 via the sealing ring 9. The filter 12 is placed in the recessed-part 11 so as to leave a gap 15 between the bottom of said recessed-part and the upper side of the filter, and also so as to form a gap between the upper edge of the tube and the underside of the filter. This enables the space 15 above the filter 11 to communicate with the column tube interior 14 through the channels 13 in the side wall of the recessed-part 11.

A slurry comprising the desired particles of separation medium is pumped into the inlet passage 7 in per se conventional manner through a flexible tube connected to the connection 6. Because of the presence of the channels 3, the slurry will pass along the side of the filter 11 and down into the column tube 1 and will continue to the outlet passage 3 in the tube bottom. The particles are retained at the bottom of the tube by the bottom filter 5, while liquid will pass essentially unimpeded through the filter. The sealing ring 9 prevents liquid/slurry from leaking along the contacting surfaces between the top element 2 and the column tube 1. Eventually, the interior 14 of the tube will have been filled with homogeneously packed particles (not shown). In the case of the illustrated embodiment, this may be seen as the pumping ceasing, by the particles clogging the channels 13 and stopping the delivery of slurry. Naturally, it is also possible to use a suitable indicator which will indicate when filling of the tube is complete, for instance a suitably positioned optical sensor which detects when the particles begin to pack at the connection 6, or a pressure sensor which detects the change in pressure that occurs when the channels 13 become blocked or clogged, etc.

Figure 2:
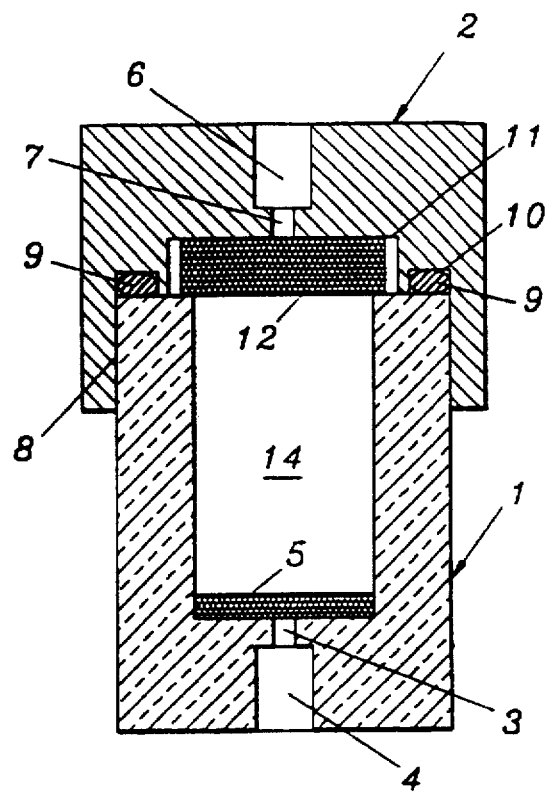
FIG. 2 is a view corresponding to the view of FIG. 1, but shows the column inlet element in a locked position after completion of a filling operation.
Figure 3:
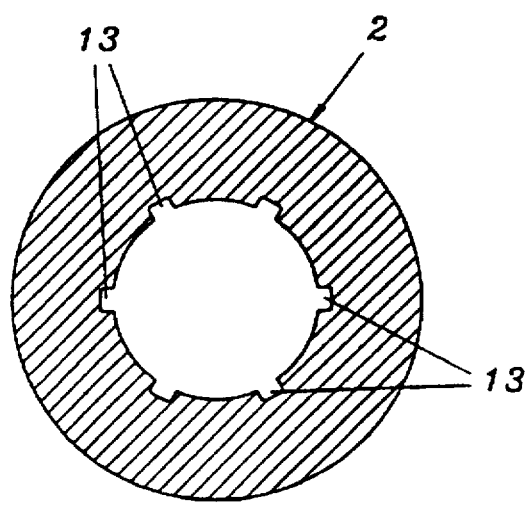
FIG. 3 is a cross-sectional view taken on the line A—A in FIG. 1.

When the column tube is full and pumping has been stopped, the top element 2 is pressed down over the column tube 1 to the position shown in FIG. 2, either manually or mechanically, and is firmly locked in this position. In this regard, the top filter 12 is compressed slightly between the top element 2 and the upper edge of the tube, so that the filter abutment surfaces will seal effectively and close the earlier open communication of the channels 13 with the column tube interior. The sealing ring 9 will have been compressed in the groove 10 at the same time, so as to ensure effective sealing against leakage when the packed column is used. The filling arrangement is then disconnected and the packed separation column is ready for use. It will be apparent that the particle bed will have the same degree of compaction as that during filling of the column tube, in other words that the stability of the particle bed achieved while filling the column tube will be retained and that this stability can be maintained even at high liquid pressures, such as in HPLC.

The top element 2 can be locked in the position shown in FIG. 2 in a number of different ways. For instance, the top element 2 may be constructed for screw-engagement with the upper part of the column tube 1, in which case the top element is brought to its sealing position by screwing said element down along the column tube. Alternatively, the top element may be provided with an internal (e.g. circular) recess which coacts with a stop shoulder (e.g. also circular) on the outside of the column tube, or vice versa. In this case, there may be provided above such a stop shoulder a further stop shoulder which functions to lock the top element temporarily in the filling position illustrated in FIG. 1. The use of cotter-pins or like devices is a further alternative.

In order to ensure that the top element 2 will be held in its sealing position (FIG. 2) in use, at least when using the stop shoulder (shoulders) alternative, it may be convenient to place a locking sleeve or the like over the top element such as to fix the element against the column tube, by preventing radial expansion. It is, of course, also conceivable for the top element itself to lack a locking function and to lock the element in its sealing position totally with the aid of an additional element instead, such as a sleeve-like element of the aforesaid kind or a similar sleeve-like element which can be placed over the top element and which includes means for locking coaction with the separation column.

Naturally, the material in the top filter 12 will need to have at least a certain degree of rigidity, in order to achieve the intended function. If the filter material used is not sufficiently rigid in this regard, appropriate supportive means may be used, for instance the filter may be placed in a cassette or like supportive device.

In order to ensure that the top filter 12 will not be pressed down against the column tube 1 by the pressure of the liquid when the top filter 12 is in its filling position (FIG. 1), and therewith prevent the passage of slurry past the filter, small spacer elements in the form of pegs or the like, for instance, may be provided on the filter surface that abuts the column tube. These pegs, or like projections, will preferably be configured to pierce the filter and/or be deformed to a sufficient extent as the filter is pressed down onto the column tube when locking the top element (FIG. 2). Such spacer elements may replace totally the frictional engagement of the filter with the side-wall of the recessed-part 11.

Although not specifically shown in FIG. 2, it will be understood that, in practice, the sealing ring 9 will be pressed against the partition wall 11a between the groove 10 and the channels 13 as the top element 2 is pressed down into its locked position, so as to deform the partition wall and press said wall against the filter 12, at least to a substantial extent. This will reduce or even essentially completely eliminate the pocket or dead volume that is formed between the channel wall and the filter in the FIG. 2 illustration.

As will be understood, in order to prevent slurry from entering the sealing groove 10 during the filling process, the inner wall 11a of the recessed-part 11 may be extended right down to the column tube 1 in the filling position, and then be deformed when the top element 2 is brought to its locked state. The bottom part of the wall may optionally extend radially inwards beneath the filter to some extent. Alternatively, the partition wall 11a may extend down into a corresponding groove in the upper side of the column tube 1 and therewith effectively prevent access to the sealing groove.

In the case of the FIG. 2 illustration, when the filter 12 is in a locked state the filter will lie against the abutment surfaces of both the top element 2 and the column tube 1. As will be understood, it may be sufficient for the top filter 12 to seal solely against one of these abutment surfaces. If desired, means may be provided for holding the filter 12 spaced from each of these surfaces, for instance spacer elements in the bottom of the recess-part 11, so as to ensure the provision of a liquid distributing space above the filter 12. Similarly, the aforesaid spacer elements on the column tube abutment surface need not necessarily be configured for piercing of the filter 12, provided that an effective seal can be achieved against the bottom-part of the recessed-part 11. Furthermore, it is not necessary for the filter 12 to be movable in relation to the top element, but may be fixed therein through the medium of spacer means.

Figure 4:
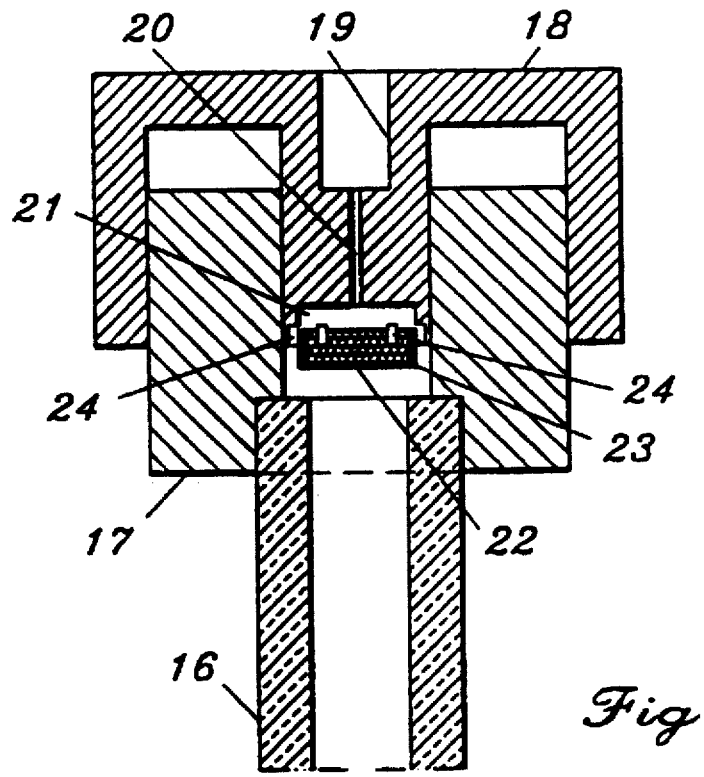
FIG. 4 is a partial longitudinal-sectioned view of another embodiment of the separation column and shows the column in a filling position.
Figure 5:
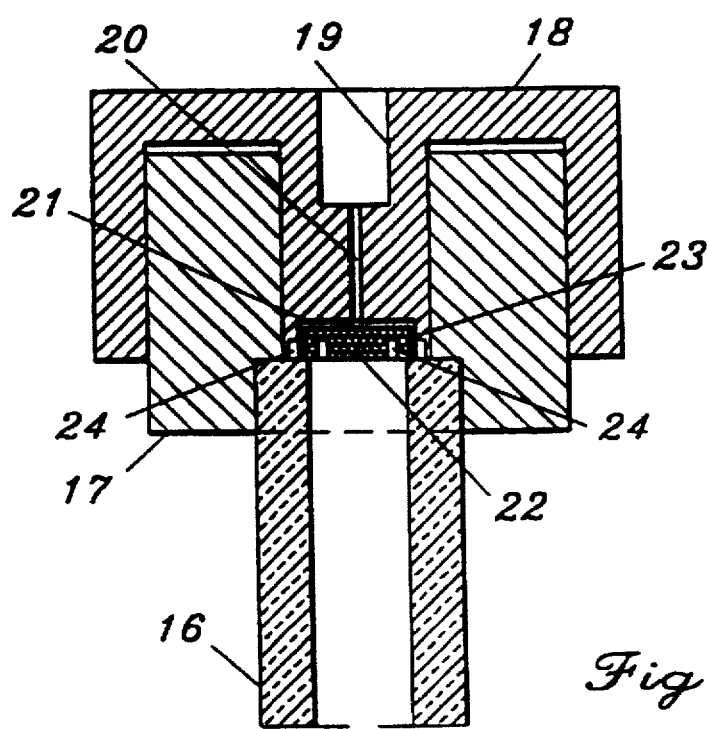
FIG. 5 is a view corresponding to the view of FIG. 4, but with the inlet part in a locked position after filling of the column has been completed.

FIGS. 4 and 5 illustrate a slightly modified embodiment of the invention. This embodiment includes a column tube 16 which is provided with an end-piece 17 having a larger inner diameter than that of the column tube. A top element 18 can be screwed onto the end piece 17 and has a connection 19 which is joined to an inlet passage 20. The inlet passage opens into a recessed-part 21 in the bottom of the top element 18 and is adapted to accommodate a top filter 22 provided with a peripheral sealing ring 23 (for instance pressed therein). A number of radial slots or apertures 24, for instance four in number, which function as bypass channels are provided in the side-edge of the recessed-part 21 that lies proximal to the column tube 16.

FIG. 4 shows the top element 18 in the filling state of the column, wherein the top filter 22 (similar to the filter 12 in the FIG. 2 embodiment) is in frictional engagement with the side-wall of the recessed-part 21 at a distance from the bottom of said recessed-part such that the channels 24 connect the space above the filter 22 with the space beneath the filter, and therewith with the interior of the column tube 16.

When the filter 22 is placed in the tube-filling or tube-packing position and the bypass channels 24 are thus open, as illustrated in FIG. 4, particle slurry is pumped into the column. When the column has been filled with packed particles, the top element 18 is screwed down to the bottom position shown in FIG. 5, while maintaining the same packing pressure. The filter 22 and the sealing ring 23 are therewith forced past the channels 24 and in towards the bottom of the recessed-part 21 of the top element, thereby closing the channels 24. In this state of the arrangement, the sealing ring 23 will thus seal between the column tube 16 and the top element 18, so that liquid can only pass through the filter 22.

In both of the aforedescribed embodiments, the bypass channels are delimited between the top filter and recesses in the top element. Naturally, the channels may be formed instead by peripheral recesses in the filter. Referring back to FIGS. 1 and 2, it is also conceivable to omit the partition wall 11a between the sealing groove 10 and the filter accommodating recessed-part 11 and allow the whole of the seal 9 to extend in towards the filter 12. This enables the channels to be formed in the seal 9 itself, these channels being blocked or eliminated by deformation as the filter is compressed when the top element is pressed to its locked position. Naturally, different combinations of these alternatives are also conceivable.

It will be obvious that the construction of the separation column, and then particularly its inlet part, can be varied in a number of different ways. The invention is therefore not limited in any way to the exemplifying embodiments specifically described above and illustrated in the drawings, since the invention will, on the contrary, include all variants that lie within the scope of the general inventive concept as defined in the following claims.

We claim:

1. A method of filling a liquid chromatographic column with particulate separation medium, which comprises: introducing a liquid suspension of the particulate separation medium into one end of the column, said column being closed at one end by a first filter so that the particles will be retained by the filter while the liquid passes therethrough; and closing the other end of the column with a second filter when filling of the column is terminated, characterized by delivering the particle suspension through an inlet element which is displaceable axially in relation to the end of the column and in which inlet element the second filter is mounted;

maintaining the inlet element and the filter during the filling process in an position in which the particle suspension is able to pass from the upper side of the filter past the side-edge of the filter to the interior of the column; and after completion of the filling process, displacing the inlet element towards the end of the column, while maintaining liquid pressure, to a position in which passage past the filter is prevented, and fixing the inlet element in this position.

2. A liquid chromatographic column which is intended to be filled with particulate separation medium and which includes a column tube having an inlet part provided with a top filter and an outlet part provided with a bottom filter, characterized in that the top filter is disposed in an inlet element which is displaceable axially in relation to the end of the column between a filling position, in which particle suspension is able to pass from the upper side of the top filter and flow past the side-edge of said filter to the interior of the column, and a lockable use-position in which passage past the filter is prevented.

3. A column according to claim 2, characterized in that the top filter seals against passage past the filter when in said use position.

4. A column according to claim 3, characterized in that in the locked use-position of the top filter in the column, the top filter seals against the upper side of the column tube.

5. A column according to claim 4, characterized in that in the locked use-position of the top filter in the column, the top filter also seals against the bottom of the inlet element.

6. A column according to claim 2 or 3, characterized in that the inlet element has a central recessed-part into which its inlet channel discharges and in which the filter can be moved axially, bypass channels extending between the wall of said recessed-part and the filter.

7. A column according to claim 6, characterized in that said bypass channels are delimited between the outer edge of the filter and radial recess in the wall of the recessed-part.

8. A column according to claim 6, characterized in that the bypass channels are provided at least partially in the filter.

9. A column according to claim 6, characterized in that the bypass channels are provided at least partially in the sealing element.

10. A column according to claim 6, characterized in that the bypass channels extend along essentially the full depth of the recessed-part.

11. A column according to claim 2, characterized in that the column includes a sealing element which is located radially outside the filter and which functions to seal between the inlet element and the column tube.

12. A column according to claim 2, characterized in that the filter is compressible and has a thickness which exceeds the depth of the recessed-part.

13. A column according to claim 2 that has been filled with a separation medium by a method of filling a liquid chromatographic column with particulate separation medium, by introducing a liquid suspension of the particulate separation medium into one end of the column, said column being closed at one end by a first filter so that the particles will be retained by the filter while the liquid passes therethrough; and closing the other end of the column with a second filter when filling of the column is terminated, characterized by delivering the particle suspension through an inlet element which is displaceable axially in relation to the end of the column and in which inlet element the second filter is mounted;

maintaining the inlet element and the filter during the filling process in an position in which the particle suspension is able to pass from the upper side of the filter past the side-edge of the filter to the interior of the column; and after completion of the filling process, displacing the inlet element towards the end of the column, while maintaining liquid pressure, to a position in which passage past the filter is prevented, and fixing the inlet element in this position.

* * * * *